(12) United States Patent
Sunshine (10) Patent No.: US 7,201,035 B2
(45) Date of Patent: Apr. 10, 2007

(54) SENSOR ARRANGEMENT

(75) Inventor: Steven A. Sunshine, Pasadena, CA (US)

(73) Assignee: Smiths Detection Inc., Pasadena, CA (US)

( * ) Notice: Subject to any disclaimer, the term of this patent is extended or adjusted under 35 U.S.C. 154(b) by 0 days.

(21) Appl. No.: 11/365,938

(22) Filed: Mar. 2, 2006

(65) Prior Publication Data

US 2006/0144123 A1 Jul. 6, 2006

Related U.S. Application Data

(62) Division of application No. 10/864,551, filed on Jun. 10, 2004, now Pat. No. 7,040,139.

(60) Provisional application No. 60/477,624, filed on Jun. 10, 2003.

(51) Int. Cl.
*G01N 37/00* (2006.01)
*H04Q 5/22* (2006.01)
*G08B 26/00* (2006.01)

(52) U.S. Cl. .................. 73/24.01; 422/98; 340/10.1; 340/10.3; 340/505

(58) Field of Classification Search ............... 73/24.01, 73/23.2, 23.34; 257/253; 338/34, 35; 340/505, 340/10.1, 10.3; 422/98
See application file for complete search history.

(56) References Cited

U.S. PATENT DOCUMENTS

| | | | |
|---|---|---|---|
| 4,543,576 A | | 9/1985 | Hieber et al. |
| 4,665,385 A | * | 5/1987 | Henderson ............. 340/539.26 |
| 4,760,351 A | | 7/1988 | Newell et al. |
| 5,117,192 A | | 5/1992 | Hurd |
| 5,597,534 A | | 1/1997 | Kaiser |
| 5,798,694 A | | 8/1998 | Reber et al. |
| 5,936,150 A | | 8/1999 | Kobrin et al. |
| 6,002,344 A | | 12/1999 | Bandy et al. |
| 6,084,503 A | | 7/2000 | Ruile et al. |
| 6,085,576 A | | 7/2000 | Sunshine et al. |
| 6,112,152 A | | 8/2000 | Tuttle |

(Continued)

FOREIGN PATENT DOCUMENTS

JP       90327442 A       12/1997

(Continued)

OTHER PUBLICATIONS

Cyrano Sciences, "Nose News", http://cyranosciences.com/press/, Revision 1.1.1.1, 2000 Cyrano Sciences Inc., pp. 1-5.

(Continued)

*Primary Examiner*—Michael Cygan
(74) *Attorney, Agent, or Firm*—Foley & Lardner LLP (57) ABSTRACT

A chemical sensing system has: an interrogation unit operable to wirelessly transmit an interrogation signal and wirelessly receive a response; an environmentally sealed container for holding a chemical analyte; a sensor array unit in fluid communication with the analyte disposed within the container, where the sensor array unit is operable to generate a response in the presence of a chemical stimulus; and a passive responder unit connected with the sensor array unit, the responder unit being powered from the interrogation signal, where the responder unit is operable to wirelessly receive the interrogation signal and wirelessly transmit the response to the interrogation signal to the interrogation unit.

10 Claims, 5 Drawing Sheets

U.S. PATENT DOCUMENTS

| | | | |
|---|---|---|---|
| 6,144,332 | A | 11/2000 | Reindl et al. |
| 6,278,379 | B1 | 8/2001 | Allen et al. |
| 6,294,997 | B1 | 9/2001 | Paratore et al. |
| 6,370,955 | B1 | 4/2002 | Tuller et al. |
| 6,392,562 | B1 | 5/2002 | Boston et al. |
| 6,592,820 | B1 | 5/2002 | Boston et al. |
| 6,641,533 | B2 | 11/2003 | Causey et al. |
| 6,658,915 | B2 | 12/2003 | Sunshine et al. |
| 6,661,339 | B2 | 12/2003 | Muirhead |
| 6,711,937 | B2 * | 3/2004 | Richards et al. ............ 73/29.01 |
| 6,718,888 | B2 | 4/2004 | Muirhead |
| 6,782,601 | B2 | 8/2004 | Smeyak et al. |
| 6,878,177 | B2 * | 4/2005 | Lohr et al. .................. 55/385.2 |
| 6,943,678 | B2 | 9/2005 | Muirhead |
| 7,040,139 | B2 * | 5/2006 | Sunshine .................... 73/23.2 |
| 2002/0098119 | A1 | 7/2002 | Goodman |
| 2004/0168618 | A1 | 9/2004 | Muirhead |
| 2005/0241548 | A1 | 11/2005 | Muirhead |

FOREIGN PATENT DOCUMENTS

| | | |
|---|---|---|
| WO | WO 00/16081 A1 | 3/2000 |
| WO | WO 03/044521 A1 | 5/2003 |

OTHER PUBLICATIONS

IBM, IBM Case study on Cyrano Sciences, Inc.—printable version, "Cyrano Sniffs Out Chemicals With Wireless Infrastructure From IBM", http://www.-306.ibm.com/software/success/cssdb.nsf, Apr. 2003, pp. 1-4.

Cyrano Sciences, "CYRANOSE 320", http://cyranosciences.com/products/cyranose.html, Revision 1.4, 2000 Cyrano Sciences Inc., pp. 1-3.

Cyrano Sciences, "NOSECHIPS™", "CHEMALERT™ (Under Development)", "CHEMBIOALERT™ (Under Development)", http://cyranosciences.com/products/Nosechip.html, Revision 1.2, 2000 Cyrano Sciences Inc., pp. 1-3.

Cyrano Sciences, "Sensor Networking", http://cyranosciences.com/products/distributedmon.html, Revision 1.2, 2000 Cyrano Sciences Inc., pp. 1-2.

Ong et al., "Monitoring of Bacteria Growth Using a Wireless, Remote Query Resonant-Circuit Sensor: Application to Environmental Sensing", Biosensors & Bioelectronics, 16 (2001), pp. 305-312.

Dominquez et al., "Performance of an Embedded Saw Sensor for Filter Bed Monitor and the Development of a Wireless Monitoring Prototype System", 1998 IEEE International Frequency Control Symposium, pp. 602-606.

Alien, "915 MHz RFID Tag", www.alientechnology.com, 2002 Alien Technology, Corp., (2 pages).

Kolnsberg et al., "CMOS Microtransceivers in Ophthalmology", pp. 249-253.

Esser et al., "Wireless Inductive Robotic Inspection of Structures", Proceedings of the IASTED International Conference, Robotics and Applications 2000, Aug. 14-16, 2000—Honolulu, Hawaii, USA, pp. 209-213.

Watters et al., "Design and Performance of Wireless Sensors for Structural Health Monitoring", CP615, Review of Quantitative Nondestructive Evaluation, vol. 21, 2002 American Institute of Physics, pp. 969-976.

Erwin M. Biebl, "RF Systems Based on Active Integrated Antennas", AEU International Journal of Electronics and Communications, vol. 57, No. 3, (2003), pp. 173-180.

Zeng et al., "Time Domain Characterization of Oscillating Sensors: Application of Frequency Counting to Resonance Frequency Determination", Review of Scientific Instruments, vol. 73, No. 12, Dec. 2002, pp. 4375-4380.

Varadam et al., "Design and Development of Passive MEMS-IDT Sensors for Continuous Monitoring of Tire Pressure", Proceedings of SPIE, vol. 4236, (2001), pp. 242-251.

Ong et al., "Wireless, Passive, Resonant-Circuit Sensors for Monitoring Food Quality", Proceedings of SPIE, vol. 4575, (2002), pp. 150-159.

Hausleitner et al., "Cordless Batteryless Wheel Mouse Application Utilizing Radio Requestable Saw Devices in Combination With the Giant Magneto-Impedance Effect", IEEE Transactions on Microwave Theory and Techniques, vol. 49, No. 4, Apr. 2001, pp. 817-822.

Ong et al., "Tracking the Harmonic Response of Magnetically-Soft Sensors for Wireless Temperature, Stress, and Corrosive Monitoring", Sensors and Actuators, A 101, (2002), pp. 49-61.

Ong et al., "A Wireless, Passive Carbon Nanotube-Based Gas Sensor", IEEE Sensors Journal, vol. 2, No. 2, Apr. 2002, pp. 82-89.

Gowens et al., "Networked Sensors: Armor for the Future Force", Proceedings of SPIE vol. 4396, (2001), pp. 1-7.

Filipov et al., "Networked Microsensor Research at ARL and the ASCTA", Sensors for Industry Conference, Nov. 2002, pp. 19-21.

Cho et al., "Wireless, Battery-Less Stethoscope for Wearable Health Monitoring", 0-7803-7419-3/02, IEEE, 2002, pp. 187-188.

Carr et al., "Integrated Pressure With Remote Power Source and Remote Readout", Transducers '95 Eurosensors IX, The 8$^{th}$ International Conference on Solid-State Sensors and Actuators, and Eurosensors IK, Stockholm, Sweden, Jun. 25-29, 1995, pp. 624-627.

Weiss, "Implications of Silicon Monolithic RFICs for Medical Instrumentation and Telemetry", 0-7803-5288-2/98, IEEE, 1998, pp. 195-204.

Hamel et al., "Micropower Peak Strain Detection Systems for Remote Interrogation", Proceedings of SPIE, vol. 3990, (2000), pp. 104-109.

Ricciardi et al., "Investigation into the Future of RFID in Biomedical Applications", Proceedings of SPIE, vol. 5119, (2003), pp. 199-209.

Neuzil et al., "Measurement and Wireless Transmission of Embedded Capacitive Microsensor's Output Using $\Sigma\Delta$ Conversion and Radio Frequency Indentification (RFID) Technology", SPIE, vol. 3044. 1997, pp. 178-185.

* cited by examiner

SENSOR ARRANGEMENT

The present invention is a divisional of U.S. application Ser. No. 10/864,551, filed Jun. 10, 2004, now U.S. Pat. No. 7,040,139 which claims priority to U.S. Provisional Application Serial No. 60/477,624, filed Jun. 10, 2003, the entire contents of which are hereby incorporated by reference.

BACKGROUND OF THE INVENTION

1. Field of the Invention

The present invention generally relates to a sensor arrangement and techniques for the detection of analytes. More specifically, the present invention relates to electronic techniques and devices for olfaction type detection/analysis, where the sensor arrangement is wirelessly connected to the processing arrangement which processes the output of the sensor arrangement, and therefore allows the sensor arrangement be hermetically isolated from the processors and/or remotely disposed with respect to the same.

2. Related Art

Techniques and devices for detecting a wide variety of analytes in fluids such as vapors, gases and liquids are known. An "electronic nose" is an instrument used to detect vapors or chemical analytes in gases, solutions, and solids. In certain instances, the electronic nose is used to simulate a mammalian olfactory system. In general, an electronic nose is a system having an array of sensors that are used in conjunction with pattern-recognition algorithms. Using the combination of chemical sensors, which produce a fingerprint of the vapor or gas, the recognition algorithms can identify and/or quantify the analytes of interest. The electronic nose is thus capable of recognizing unknown chemical analytes, odors, and vapors.

In practice, an electronic nose is presented with a substance such as an odor or vapor, and the sensor converts the input of the substance into a response, such as an electrical response. The response is then compared to known responses that have been stored previously. By comparing the unique chemical signature of an unknown substance to "signatures" of known substances, the unknown analyte can be determined. A variety of sensors can be used in electronic noses that respond to various classes of gases and odors.

A wide variety of commercial applications are available for electronic noses including, but not limited to, environmental toxicology and remediation, biomedicine, such as microorganism classification or detection, material quality control, food and agricultural products monitoring, heavy industrial manufacturing, ambient air monitoring, worker protection, emissions control, and product quality testing. Many of these applications require a portable device because they are located in the field or because they are inaccessible with respect to larger laboratory models.

While handheld electronic nose devices are commercially available, they generally require the device to be in close proximity with the analyte. In certain circumstances, where the analyte is potentially a hazardous compound, the requirement of close proximity can potentially expose the operator of such a device to hazardous conditions. While it may be desirable to break up the sensing array subunit from the processing subunit, such an option is difficult to implement, primarily due to the power requirements of the sensor array unit, as well as the need to maintain a direct electrical connection between the sensor array and the remainder of the sensing device.

On the other hand, in an unrelated area of industry, remote, so called "passive" identification has flourished. An implementation of passive identification technology includes radio-frequency tags. Radio-frequency ("RF") tags have been used by industry for many years. Common uses include identification of rail cars, automobiles, cattle management and salmon returning to spawn in the Columbia River, as well as embedding the tiny tags under the skin of a pet to identify a lost dog or cat. Many people encounter RF tags when a store clerk removes theft-deterring devices from expensive clothing items.

RF and other passive tags have enabled a method of identifying items from a distance, commonly called RFID, or radio frequency identification. RIFD systems generally comprise two components, namely transponders which are attached to the items to be labeled, and readers for reading the identity of the transponders. In some cases the transponders might be programmed to broadcast data representing their identity, while in other cases, it might be an ON/OFF state such as is used in electronic article surveillance systems commonly used for anti-shoplifting in retail stores. RFID systems use small tags that contain information about the object to which the tag is attached. In its simplest form, a radio-frequency tag is a small electronic circuit board. It contains a suitable antenna and/or coil. The tags store data, such as the identification number correlating to an item. The tag being a passive device does not require a battery. A device called an interrogator or a reader is used to read the tags. The interrogator includes another electronic circuit, typically larger than the tag, that contains an antenna and a transceiver. The antenna emits radio waves which are received by the RF tag, and which is energized thereby. The tag transmits its stored, encoded data back to the interrogator wherein it is decoded.

While RFID technology and electronic article surveillance have seen many advances, the tag technology has generally been limited to rather simplistic arrangements which merely issue prestored data in response to an interrogation signal sent by an interrogation unit.

There is, therefore, a need to extend RFID technology to include more intelligent arrangements such as a versatile robust chemical sensing system for obtaining information pertaining to an analyte (e.g. presence, concentration, etc.) in various diverse test samples/environments via a wireless/remote query, without requiring a hardwired connection between the sensing elements and the data processing arrangement.

BRIEF SUMMARY OF THE INVENTION

The present invention uses these two unrelated technology areas to provide a passive chemical sensor system where the sensing unit is wirelessly/remotely located from the processing unit and where the sensing unit does not require its own self-contained power source.

More specifically, a first aspect of the invention resides in a sensor arrangement, comprising: an interrogation unit operable to wirelessly transmit an interrogation signal and to wirelessly receive a response; a container configured to be environmentally sealed and for holding a chemical analyte; a sensor unit in fluid communication with the analyte disposed within the container, the sensor unit being configured to respond to the analyte; and a responder unit connected with the sensor unit, the responder unit and the sensor unit being respectively powered by the interrogation signal, the responder unit being operable to wirelessly transmit to the interrogation unit a signal indicative of the sensor unit's response to the analyte.

In the above arrangement the responder unit comprises an antenna configured to respond to the interrogation signal to produce an electrical signal that enables the responder unit and the sensor unit. Thus, the responder unit is a passive arrangement. It can include an integrated circuit. The sensor array unit and the passive responder unit may be combined in a single integrated circuit.

Preferably, the response which is generated by the sensor unit is a measurable electrical property such as a voltage or can take the form of an electromagnetic signal. The interrogation unit or interrogator, as it will be sometimes referred to, preferably includes a transceiver and can be a handheld device.

The above mentioned sensor unit comprises a plurality of sensors which form a sensor array wherein each sensor in the sensor array is a member selected from the group consisting of a bulk conducting polymer film, a semiconducting polymer sensor, a surface acoustic wave device, a fiber optic micromirror, a quartz crystal microbalance, a conducting/nonconducting regions sensor, a dye impregnated polymeric coatings on optical fiber or combinations thereof. Preferably, the responder unit further includes one of a transmitter and a transceiver, and the interrogation unit can further comprises processing circuitry which processes the response received by the interrogation unit to identify the analyte.

Preferably, the interrogation unit can include a device for receiving an input from an operator, and a device for providing an output to an operator. In given embodiments, the interrogation unit and the sensor array unit are inductively coupled. Alternatively, the interrogation unit and the sensor array unit may be capacitively coupled.

A further aspect of the invention resides in a sensing method, comprising: placing a sample comprising an analyte in a container; closing the container and enclosing a sensor array therein; exposing the sensor array to the sample; using an interrogation unit to wirelessly transmit an interrogation signal to a responder unit operatively connected with the sensor array; powering the responder unit and the sensor array unit, using the interrogation signal; generating a response indicative of the analyte as sensed by the sensor array; and wirelessly transmitting the response to the interrogation unit using the responder unit. Alternatively, the sample may be suspected of containing an analyte or a threshold amount thereof.

In this method, exposing the sensor array to the analyte allows sensor elements of the sensor array to react to the analyte. Further, the step of locating the sensor array in the container is such that it is exposed to a gaseous medium in the container.

Preferably, the above-mentioned method includes processing the wirelessly transmitted response from the responder unit, to identify the analyte. In this case the step of generating the response can include generating a measurable electrical property.

A further aspect of the invention resides in a sensor arrangement comprising: a container configured to receive a sample and to be closed to retain the sample therein; a sensor arrangement disposed within the container and configured to be exposed to a gaseous medium in the container which gaseous medium contains an analyte which has a predetermined relationship with a sample introduced into the container; and an antenna and transmitter arrangement disposed within the container, the antenna being configured to be responsive to an electromagnetic signal generated externally of the container to produce sufficient electrical energy to activate the sensor array and a transmitter coupled to the sensor array and to induce the emission of a signal indicative of the analyte in gaseous medium as sensed by the sensor array.

Preferably, the above arrangement further includes an interrogator configured to wirelessly communicate with the sensor arrangement and to wirelessly excite the sensor arrangement to emit the signal indicative of the analyte. The interrogator and may be portable and may be handheld.

The above mentioned interrogator, in addition to being portable, can be configured to store the emitted signal indicative of the analyte, and can be configured to display the nature of the analyte upon it being determined. The interrogator may be configured to wirelessly relay to a remote host device the data contained in the emitted signal indicative of the analyte. Further, the interrogator can be also configured to scan an external surface of the container and derive data relating to the container and/or its contents.

Yet another aspect of the invention resides in a sensor arrangement comprising: a sensor device configured to be exposed to an analyte in a gaseous medium; and an antenna and a transmitter arrangement operatively connected with the sensor device, wherein the antenna is configured to be responsive to a wirelessly transmitted interrogation signal to produce sufficient electrical energy to activate the sensor device and the transmitter coupled to the sensor arrangement and to induce the emission of a signal indicative of an analyte as sensed by the sensor device.

In accordance with this aspect of the invention, at least the sensor arrangement is configured to be disposed in a container, and the container is configured to retain a sample in a manner wherein the sensor is exposed to a space in the container in which the gaseous medium collects. The vapor in the space comprises the gaseous medium which comprises the analyte.

In addition, the interrogation signal is produced by an interrogator device which is configured to receive and decipher the signal indicative of the analyte as sensed by the sensor array. The interrogator device can be configured to relay to a host device data contained in the signal indicative of the analyte as sensed by the sensor array. The communication between the interrogator and the host is a wireless communication.

BRIEF DESCRIPTION OF THE DRAWINGS

A more complete understanding of the exemplary embodiments of the invention will be derived from the following detailed description taken in conjunction with the accompanying drawings wherein.

DETAILED DESCRIPTION OF THE EXEMPLARY EMBODIMENTS

In general, the embodiments of the present invention relate to a chemical sensing system using sensing devices that are wirelessly connected with the associated pick-up/receiver and processing units that are used for chemical analyte sensing and monitoring.

More particularly, the invention relates to a novel wirelessly connected arrangement that has sensing elements that respond to an analyte or analytes.

This novel sensing structure may be used to sense the presence, concentration, or absence of chemical elements and compounds (whether useful or unwanted/contaminating in a liquid, gas, or plasma state), pH levels, germs (bacteria, virus, etc.), enzymes, antibodies, and so on in a number of environments such as biomedical applications (whether in vivo or in vitro), within medical test samples, food quality/inspection (whether measuring moisture within sealed packing or outside of packaging), monitoring of heavy metals found in water (groundwater, treated water, or wastewater flowing in natural waterways, canals, or pipes), and monitoring of solid or gas manufacturing waste, etc. This new, versatile sensing apparatus and method marries the techniques of radio frequency based identification with those of chemical sensor arrays, such as those used for artificial olfactometry.

Figure 1:
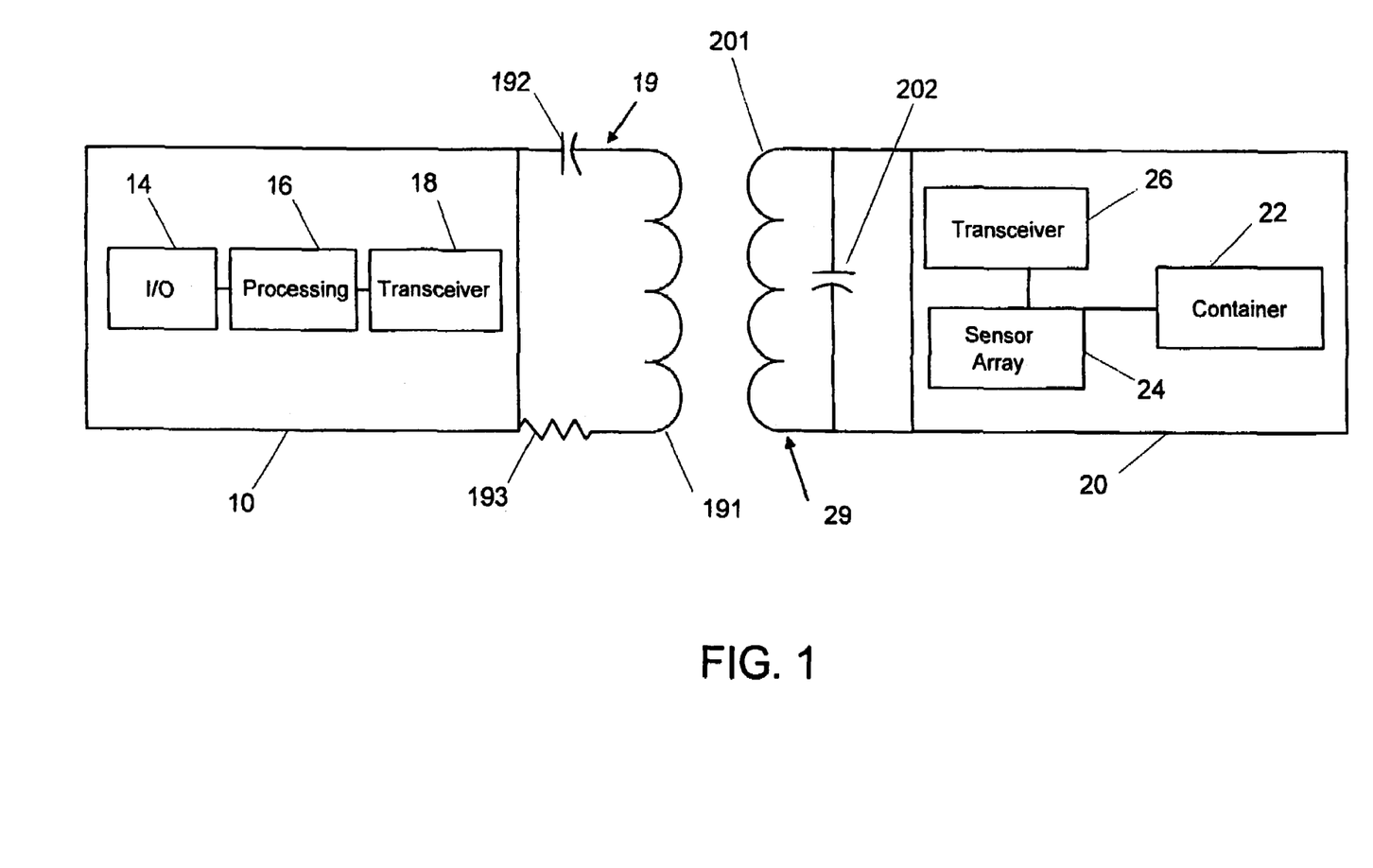
FIG. 1 is a block diagram which schematically depicts a wireless, passive chemical sensor system in accordance with an embodiment of the present invention.

FIG. 1 schematically depicts a passive, wireless chemical sensor system in accordance with an embodiment of the present invention. It will be understood that the term "passive" is used in this disclosure to refer to an arrangement which needs to be activated from a "slumbering" or inactive state via the wireless transmission of an interrogation signal thereto. This system comprises an interrogation unit 10 and a sampling unit 20. The sampling unit 20, in this embodiment, includes a sealable container 22 that is used to hold a sample including an unknown analyte that is to be identified by the chemical sensor. A sensor or sensor array 24 is in fluid communication with an interior space of the container 22. This communication while being normally a constant communication is not limited thereto and it is within the scope of at least one embodiment of the invention to arrange this communication to be selectively interruptible if so desired.

Each sensor in the sensor array unit may include a conducting polymer film, a semiconducting polymer sensor, a surface acoustic wave device, a fiber optic micromirror, a quartz crystal microbalance, a conducting/nonconducting regions sensor, a dye impregnated polymeric coatings on optical fiber and/or combinations thereof.

In an exemplary embodiment, the sensor array, consists of a plurality of individual thin-film carbon-black/polymer composite so called "chemiresistors" which are configured so as to be simultaneously/serially exposed to the analyte. The sensor array 24 is used to generate an output (which comprises a plurality signals from each of the chemiresistors) when exposed to an analyte. This output is used to identify the analyte using a data analysis technique such as that which uses data analysis algorithms.

These chemiresistors include a composite material of conductive carbon black homogeneously blended throughout a nonconducting polymer. The detector materials are deposited as thin films on an alumina substrate and are each provided with two electrical leads to create a conducting chemiresistor.

When the composite material is exposed to a vapor-phase analyte, the polymer matrix acts like a sponge and "swells up" while absorbing the analyte. The increase in volume is concomitant with an increase in resistance because the conductive carbon-black pathways through the material are broken. When the analyte is expelled, the polymer "sponge" off-gasses and "dries out". This causes the film to shrink and the conductive pathways are reestablished. The baseline resistance (Rbaseline) of the device is measured while a representative background vapor is exposed to the array. The response from the chemiresistor during an analyte exposure is measured as a bulk relative resistance change (Rmax/Rbaseline). Since an analyte will absorb into the different polymer matrices to different degrees, a pattern of response is observed across the array.

The polymer matrix "swells up" because analyte vapor absorbs into the film to an extent determined by the partition coefficient of the analyte. The partition coefficient defines the equilibrium distribution of an analyte between the vapor phase and the condensed phase at a specified temperature. This is expressed as:

$$K = C_s/C_v$$

where $C_v$ is the concentration of the analyte in the vapor phase, and $C_s$ is the concentration of the analyte in the condensed phase, which is also proportional to the detector's response. Therefore, the larger an analyte's partition coefficient, the more it will absorb into a polymer film, and the larger will be the detector's response.

Each individual detector element requires a minimum absorbed amount of analyte ($C_{s,min}$) to cause a response noticeable above the baseline noise. However, the minimum vapor concentration ($C_{v,min}$) needed to produce $C_{s,min}$ is different for each analyte since the partition coefficient is different for each analyte. Moreover, it can be shown with standard thermodynamic arguments, that the magnitude of response of an individual detector can be predicted to first order by the fractional vapor pressure exposed to the detector irrespective of the analyte identity. Therefore, the general detection limit of a sorption device is best expressed as a minimum fraction of equilibrium vapor pressure rather than a concentration value.

This behavior explains why sorption devices are rather insensitive, in terms of concentration, to high vapor pressure analytes like methane (which is a gas at ambient temperatures) and diethyl ether, but show good sensitivity, in terms of concentration, to low vapor pressure compounds exposed at low concentrations such as volatile fatty acids. For example, if the limit of detection were 0.1% of an analyte's vapor pressure, this would indicate a detection limit of 74 ppm for ethanol, but only 0.5 ppm for nonanal (a common taint in packaging materials) at 24° C. All analytes will have roughly the same limit of detection when expressed as a fractional vapor pressure.

The differences between detector responses when exposed to a given analyte—which are required to uniquely identify that analyte by providing a unique response pattern—are due to differences in chemical interactions between the analyte and the detector films. Therefore, the limit of discrimination between two analytes exposed at the same fractional vapor pressure is determined by their relative collective chemical differences across the array. Generally, chemical diversity should be very high in the polymers comprising the array detectors for a general-purpose electronic nose. Moreover, for well-defined applications, the polymers used in the detector array can be chosen to maximize chemical differences between target analytes to increase the discrimination power of a smaller array.

The composite sensor technology as implemented by the embodiments of the present invention are very effective in identifying analytes, because they are not reliant on any particular polymer type or limited to a particular set of polymers. Additionally, the simplicity of signal transduction (merely reading resistance values) and the low materials cost of the detectors (composites made of carbon black and generic polymers) makes this an ideal technology for a low-cost, hand-held, electronic nose.

The sensor array 24 is coupled with a transceiver 26. The sensor array 24 and the transceiver 26 functions in a manner similar to a transponder, in that the sensor array is normally off until the transceiver 26 receives an interrogation signal transmitted by the interrogation unit 10. The sampling unit 20 is coupled to the interrogation unit 10, whereby the sensor output data from the sensor 24 is supplied to the interrogation unit 10. As will be described below, data is transmitted from the sampling (or sensing) unit 20 to the interrogation unit 10. The interrogation unit 10 receives the sensor output data from the sensing unit 20 and either processes the data itself, stores it locally for later downloading, or transmits the data to another unit for further processing.

The sampling or the sensing unit 20 via the transceiver 26 is able to communicate with the interrogation unit 10 through the use of a wireless data transmission technique such as a radio frequency signal. With this approach, wireless, contactless reading of the chemical sensor array 24 is accomplished. Such communication provides one important advantage of this embodiment of the present invention, since the reading of the chemical sensor array is accomplished by minimizing/eliminating contact between the operator and the analyte.

For example, once the sensor array response is transmitted to the interrogation unit, the sealed container holding the analyte can be safely disposed of and/or placed in storage for further reference.

In the arrangement illustrated in FIG. 1, the interrogation unit 10 includes, merely by way of example, a transceiver 18 which is coupled to a processing subunit 16. The processing unit 16 receives the sensor output signals and processes it to determine the identity of the analyte. The interrogation unit 10 also includes input and output subunits 14 that are used to communicate information to the user of the interrogation unit. In one embodiment, the interrogation unit 10 is a handheld device.

The sensing unit may be powered by the interrogation signal issued by the interrogation unit 10. Thus, the sensing unit 20 does not require a battery or other form of self-contained power source. Because no battery is needed, the sensing unit 20 may be stored and used requiring little or no maintenance.

Further details of the sensor array, its methods of manufacture as well as the processing of its output by the processing unit are provided in U.S. Pat. No. 6,495,892, entitled: "Techniques and Systems for Analyte Detection"; U.S. Patent Application Publication No. US 2002/0098119 A1, entitled: "Electronic Techniques for Analyte Detection," and U.S. Pat. No. 6,422,061, entitled: "Apparatus, Systems and Methods for Detecting and Transmitting Sensory Data Over a Computer Network," the disclosures of which are hereby incorporated by reference herein in their entirety for all purposes.

In operation, the interrogation unit 10 transmits a signal wirelessly to the sensing unit 20. The signal is received by an antenna which converts the signal into an electrical signal. This electrical signal is used to power up the transceiver and to pass a small current through each of the resistor elements (chemiresistors) which comprise the sensor array. The transceiver can include a microchip which memorizes the voltage signals output by the sensor elements of the sensor array and stores them ready for transmission to the interrogation unit 10.

Once the interrogation unit 10 has received a data transmission from the sensing unit 20, the interrogation unit may do all the necessary processing locally, or it may in turn transmit the sensor output data on to a further device, such as a host computer for further processing. Once the interrogation signal ceases to be received by the antenna of the sensor unit 20, the sensing unit returns to its normally off or powered down state.

In certain embodiments, the sensing unit 20 includes a power supply system including a storage device to store electrical power generated by the receipt of the interrogation signal and thus enable the sensing unit to continue functioning even in the absence of the interrogation signal.

The sampling or sensing unit 20 and the interrogation unit 10 may be coupled together either inductively or capacitively. With inductive coupling, the sensing unit is powered by the electromagnetic field generated by the interrogation unit. The sensing unit's antenna picks up the electromagnetic energy to communicate with the interrogation unit. The sensing unit modulates the electromagnetic field in order to generate and transmit the sensor array data back to the interrogator unit. The data is processed by the interrogation unit or sent to another device or a host computer for further processing. In inductively coupled units, a metal coil made of copper or aluminum wire is wound into a circular pattern and is connected with the transceiver 26. The coil also acts as the sensing unit's antenna.

Capacitively coupled units are able to reduce the cost of the system, by doing away with the metal coil and use a small amount of silicon to perform the same function as the inductively coupled units. In a capacitively coupled unit, by using an electrically conductive ink instead of metal coil, a cost reduction is realized. Capacitively coupled units are also powered by the electromagnetic field generated by the interrogation unit.

The interrogation and the sensing units may also be coupled using various different industrially available standards. These include: acoustic magnetic, electromagnetic, medium RF, and microwave. The acoustic magnetic coupling is based on the principles that by exciting a strip of amorphous magnetic material that is also mechanically stressed, with a low frequency magnetic field, the strip will emit harmonics of the scanning or interrogating signal, allowing the harmonics to be detected and hence provide a detection and sensing system. In the electromagnetic coupling, the sensing unit includes a magnetic material which is illuminated by a pulse of energy, and the decay of the energizing field is monitored by the interrogation unit. In medium RF coupling, the sensing unit comprises a tuned circuit that is tuned to the frequency of the scanning system, typically between 6 MHz and 10 MHz. The interrogator unit's transceiving antenna is made by printing conductive circuitry on either side of a plastic film, and interconnecting the two surfaces. The sensing unit's circuit resonates at the interrogating frequency when in the presence of the interrogator. With microwave coupling, the interrogator and the sensing unit are coupled via microwave radiation.

In addition to medium RF coupling, other RF coupling means are also suitable for coupling the interrogator and the sensing unit. These RF coupling technologies include low frequency and high frequency couplings. Using low frequency, the sensor unit and the interrogator communicate with one another using frequencies in the kHz range (e.g., 125 kHz, 134.2 kHz, and so on). The advantage of using low frequency technology is that it will result in a less expensive system, however the system will tend to have a shorter effective range. Using high frequency, the sensor unit and the interrogator communicate with one another using frequencies in the MHz to GHz range (e.g., 13.56 MHz, 400 MHz, 2.5 GHz, 5.8 GHz, and so on). The advantage of using a high frequency design is that the system will have a longer range, but will tend to be more expensive. Yet alternately, the interrogation unit and the sensor unit can communicate over the combined low and UHF frequencies (e.g., 134.2 kHz to 903 MHz, and so on).

Various embodiments use RF coupling to link the interrogator and the sensing system, as it relates to either unit's transceiver coil or antenna design. In FIG. 1, the sensing unit 20 is illustrated in communication with the interrogator 10. The interrogator 10 includes a transceiver 18 and an antenna circuit 19 that emits electromagnetic waves that are used to provide an interrogating field to the sensing unit 20. The antenna circuit 19 includes, in the illustrated arrangement, an inductor 191, a capacitor 192 and a resistor 193. The resistor 193 may further include a variable resistor.

The sensing unit 10 further includes an antennal circuit 29 which includes an inductor 201 and a capacitor 202. The interrogating field provided by the interrogator 10 induces a current in the inductor 201 which charges the capacitor 202 that is used to provide power to the sensing unit 20. After being powered up, the sensing unit's sensor array generates an output in response to being exposed to the analyte and transmits the sensor array data via the antenna circuit 29 to the interrogator 10. The sensor unit 20 and the interrogator unit may both include a memory circuit for the storage of information derived using the sensor array output.

In the arrangement illustrated in FIG. 1, the antenna arrangements are dual purpose antenna, wherein the same antenna is used to send the interrogation signal and receive the sensor output. The advantage of a dual purpose antenna is that it tends to be lower in cost and allows for a more compact overall size. The disadvantage of a dual purpose antenna is that it tends to have a shorter range and have a limited impedance matching.

Accordingly, in an alternate embodiment, the transceiver uses a dual antenna, where different receive and transmit antennas are used. A dual antenna embodiment allows for a longer range, but tends to be more expensive and somewhat larger. Suitable shapes for the transmit/receive antennas include conductive coils, spirals, elongated wires and cables, and so on. The interrogation unit's field generating antenna establishes an alternating electromagnetic field of desired frequency and amplitude in the environment surrounding the sensing unit or at least the sensing unit's antenna. The amplitude of the field necessary to generate a predetermined signal level (sensor amplitude response) will vary depending upon system parameters such as coil size, electric characteristics of the resonant circuit, and sensitivity of receiving electronics in the interrogation and sensing units.

Furthermore, the specific type of antenna used to detect emissions from any one, or several, of the sensor units will depend upon (among other things) the type of emission being received, the distance the emissions travel, and physical design of the receiving antenna. For example, a sensing apparatus designed for detecting electromagnetic emission considered in the low frequency range (up to about 20 MHz) must be paired with a suitable electromagnetic pick-up coil located up to a kilometer from the sensing structure; whereas, if the emissions must travel a much greater distance (several kilometers—such as that from a satellite), the equipment preferably must be capable of operation at higher frequencies (above 20 MHz to the 80 GHz range). Antenna technology for designing an electromagnetic send/pick-up antenna suitable for use and capable of operating up to 80 GHz is readily available.

Figure 2:
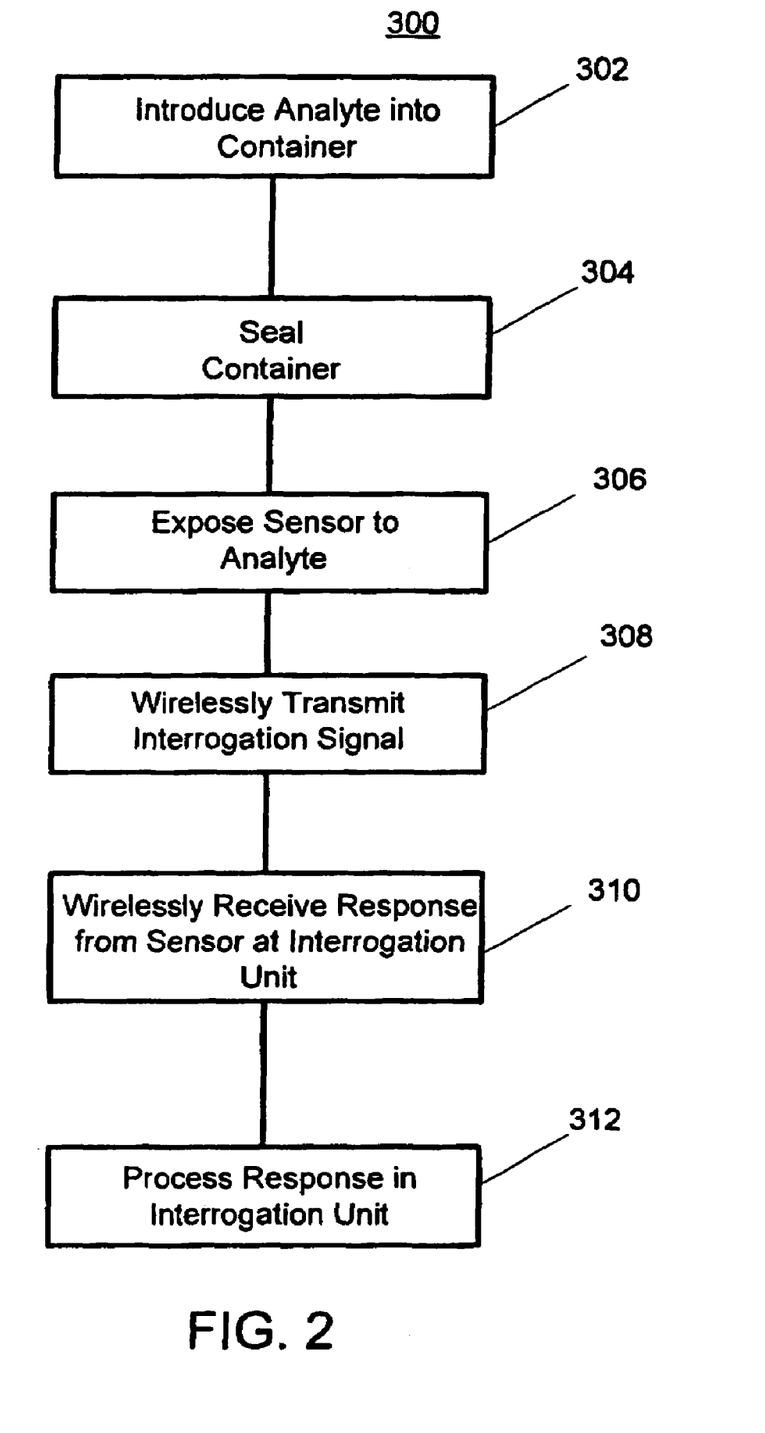
FIG. 2 is a block diagram of a method of sensing an analyte in accordance with another embodiment of the present invention.

FIG. 2 is a block diagram 300 depicting a method of sensing an analyte in accordance with an embodiment of the present invention. First, a sample containing an unknown analyte is placed in a container (step 302). The container is then sealed, such as for example, by placing a cap on the container (step 304). The container's cap includes the remainder of the sensing unit 10 described in FIG. 1 above. Once the container is sealed, the sensor array is exposed to the analyte (step 306) either by diffusion, convection and/or by movement of the sealed container. Next, the interrogator is used to wirelessly transmit a signal to the sensing unit (step 308). Next, the signal is received by the sensing unit's antenna. The received signal (1) powers up the sensing unit; (2) causes the sensor array to generate an output signal corresponding to the analyte; and (3) causes the sensing unit's transceiver to wirelessly transmit the sensor array output signal back to the interrogation unit. The sensor array output signal is received by the interrogation unit (step 310) and then the interrogation unit processes the sensor signal to identify the analyte (step 312).

In addition to the embodiments described above, other embodiments wherein the interrogation unit wirelessly communicates with the sensor element/array/unit in the sensing system provide features as follows:

(a) The sensing unit may be used for one-time (e.g., disposable) operation, or periodic operation.

(b) The system may be used for operation within a wide range of testing environments such as biomedical applications (whether in vivo or in vitro), within medical test samples, food quality/inspection (within or outside of sealed packing), monitoring of contaminants in water (groundwater, treated water, or wastewater flowing in natural waterways, canals, or pipes), and monitoring of gases/aerosols. The sensing structure can be driven by having the current be induced in the sensing structure by an electromagnetic field(s) generated using a remote coil in the interrogator.

(c) Several sensing units may be incorporated into an array to provide a package of sensing information about an analyte, such as, analyte composition, and the concentration of constituent components/elements of the analyte in which the analyte(s) is found.

(d) A unit having the capacity to generate an interrogation field, as needed, as well as the capacity to receive signals emitted from several sensing structures wherein each of the emitted signals have a characteristic operating range or frequency allowing each to be distinguished from the other, may be used. This wide-band capability, of course, requires either the use of broadband antennas, such as spiral antennas, or multiple narrowband transmitting and receiving antennas. Inasmuch as this technology is known to those skilled in the art of antenna theory and design, no further description is deemed necessary.

Figure 3:
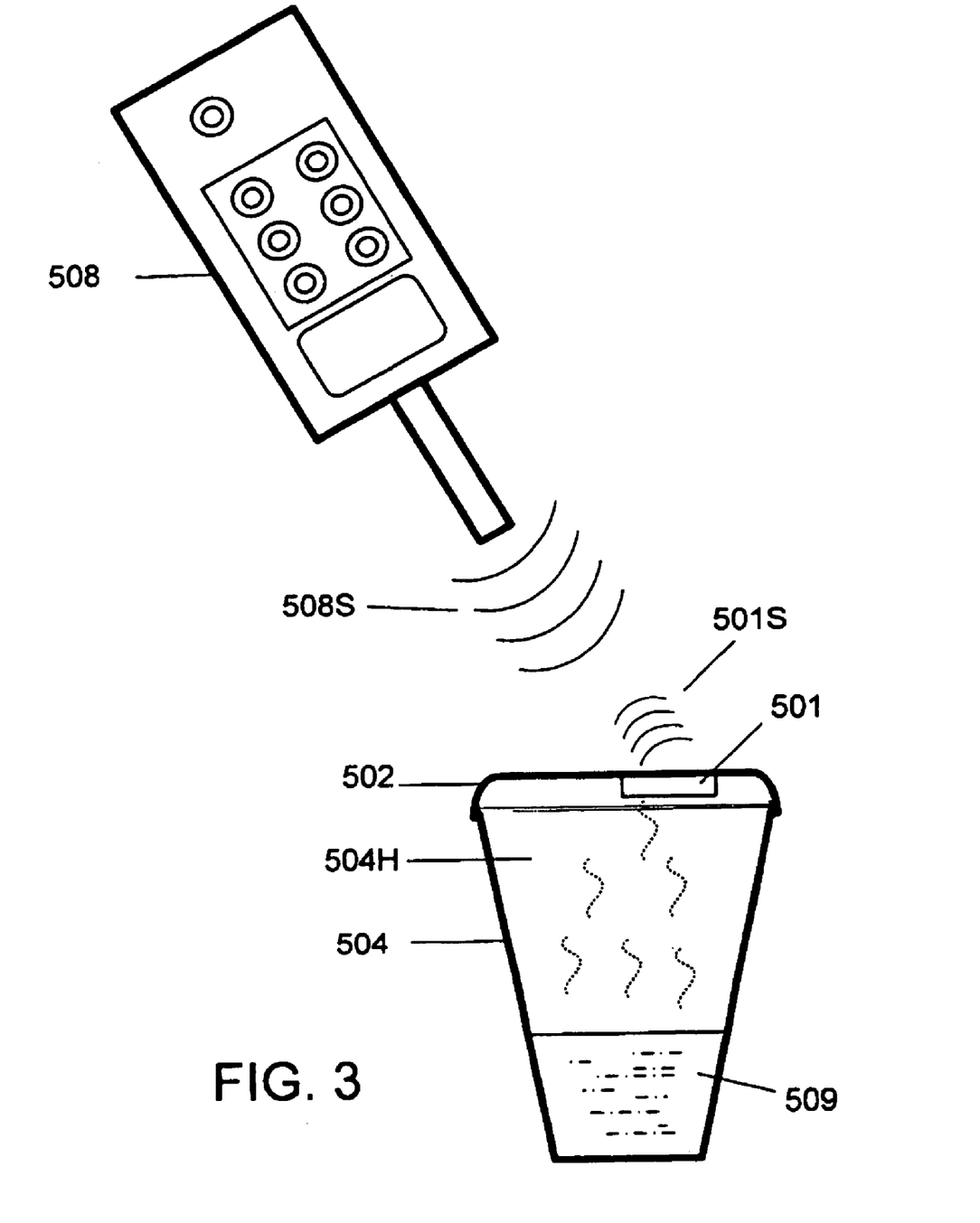
FIG. 3 is a schematic depiction of a hand-held interrogator extracting information from a sensor arrangement which is enclosed in a container in which an sample has been disposed and wherein the sensor arrangement has been exposed to the vapors emitted from the sample.

FIG. 3 shows another embodiment of the invention wherein the sensor unit 501 (e.g. sensor array, antenna and transmitter/transceiver) is disposed in the lid 502 of a container 504 such as specimen cup, and wherein the interrogator 508 comprises a hand-held arrangement which can be brought in proximity of the sealed container (specimen cup/lid). The disposition of the sensor unit 501 on the underside of the lid 502 enables the sensor to be supported in a "head space" 504H of the container 504 and thus exposed to vapors (analyte) which has a predetermined relationship with a sample 509 sealed within the container 504. It will be noted that the sample is illustrated as being a liquid. However, the sample is not so limited and can be solid, semi-solid (e.g., gel/past) or even gas (e.g., a sample of contaminated air, a sample of a person's breath or the like).

This arrangement permits the sensor unit 501 in the lid 502 to be exposed to the analyte and activated via a wirelessly transmitted interrogation signal 508S from the interrogator 508 and for the signal 501S which is subsequently generated by the sensor unit 501 to be received by the interrogator 508.

By permitting the interrogator 508 to be held in relative close proximity to the sensor unit 501, the power of the interrogation signal 508S can be reduced to reduce noise in an environment such as a hospital wherein pacemakers and/or the like type of sensitive electronic equipment can be affected and/or in situations wherein detection of the interrogation signal is not desired.

The direction of the interrogation signal 508S can also be limited in given embodiments so that, in the event that there are multiple samples each disposed in a container and wherein the containers have been collected together, each of the containers can be interrogated individually without cross-talk from those nearby. This arrangement enables the transmitting arrangement which form part of the sensor units to be the same and thus reduce both complexity and cost.

This type of arrangement, by way of example, finds application in screening athletes at a meet for drug use. Each container can take the form of a specimen cup containing a urine sample. By being able to selectively read the output of each of the sensor units 501 disposed in the lids of the specimen cups, it is possible to screen a plurality of specimens within a short period of time. This would be useful, e.g., testing employees for drug abuse. A similar procedure can be carried out in hospitals wherein screening for diabetes (for example) is being carried out.

Figure 4:
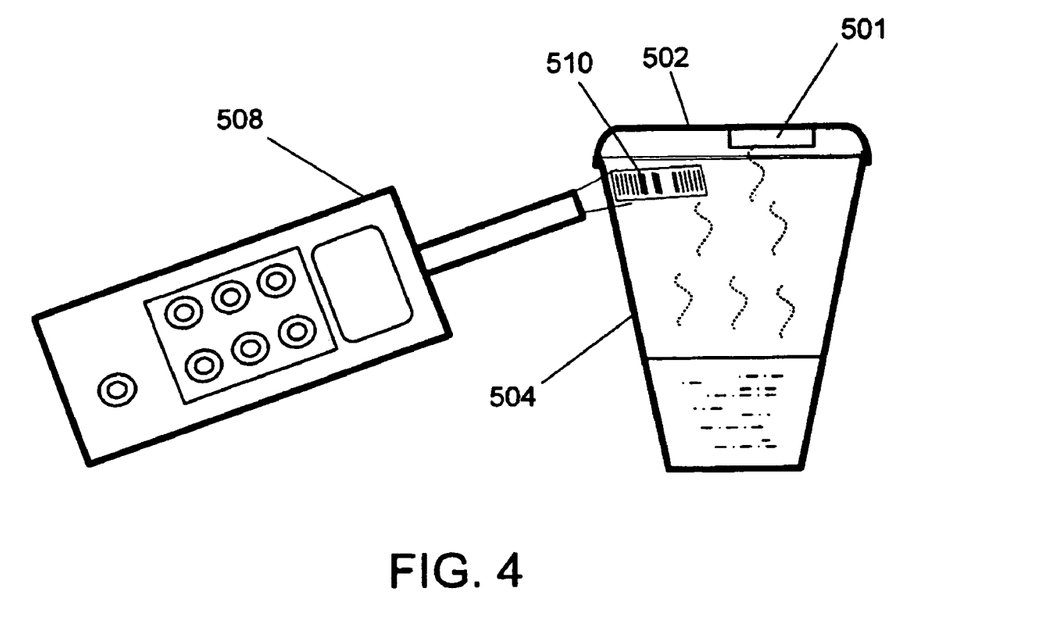
FIG. 4 is a view similar to the that shown in FIG. 3, but wherein data which has been transmitted to the interrogator from the sensor arrangement is subsequently relayed to a host device such as a main frame or the like type of device capable of interpreting/collating data which has been gleaned from the sensor.

It is, as shown in FIG. 4, also within the scope of the present invention to be able to also collate the output of the sensor unit 501 within the container/cup with other data such as patient data and/or data designed to permit anonymity. By rendering the interrogator 508 multi-functional in this manner, it is possible for an embodiment of the invention to not only wirelessly interrogate a sensor unit 501 for data pertaining to a sample isolated within a container, but also collect and collate data through such means and the provision of a visible/non-visible bar-code 510 on the container and the inclusion of bar code reader or the like in the interrogator 508.

It should be appreciated that the size of the container is not limited to cups and the like and should be taken to include those which provide an enclosed head space in which analyte containing vapor can collect, such as cargo containers for aircraft, shipping containers for delivery by container ship/rail or even rooms. For example, a sensor unit can be used to detect an analyte which is given off by explosives or the like type of weapon/contraband. By disposing such a sensor or a series of such sensors in the cargo pod, such as used in commercial aircraft, the presence of materials which have not been detected by other forms of screening and which are dangerous, may be rendered detectable and appropriate action taken.

Figure 5:
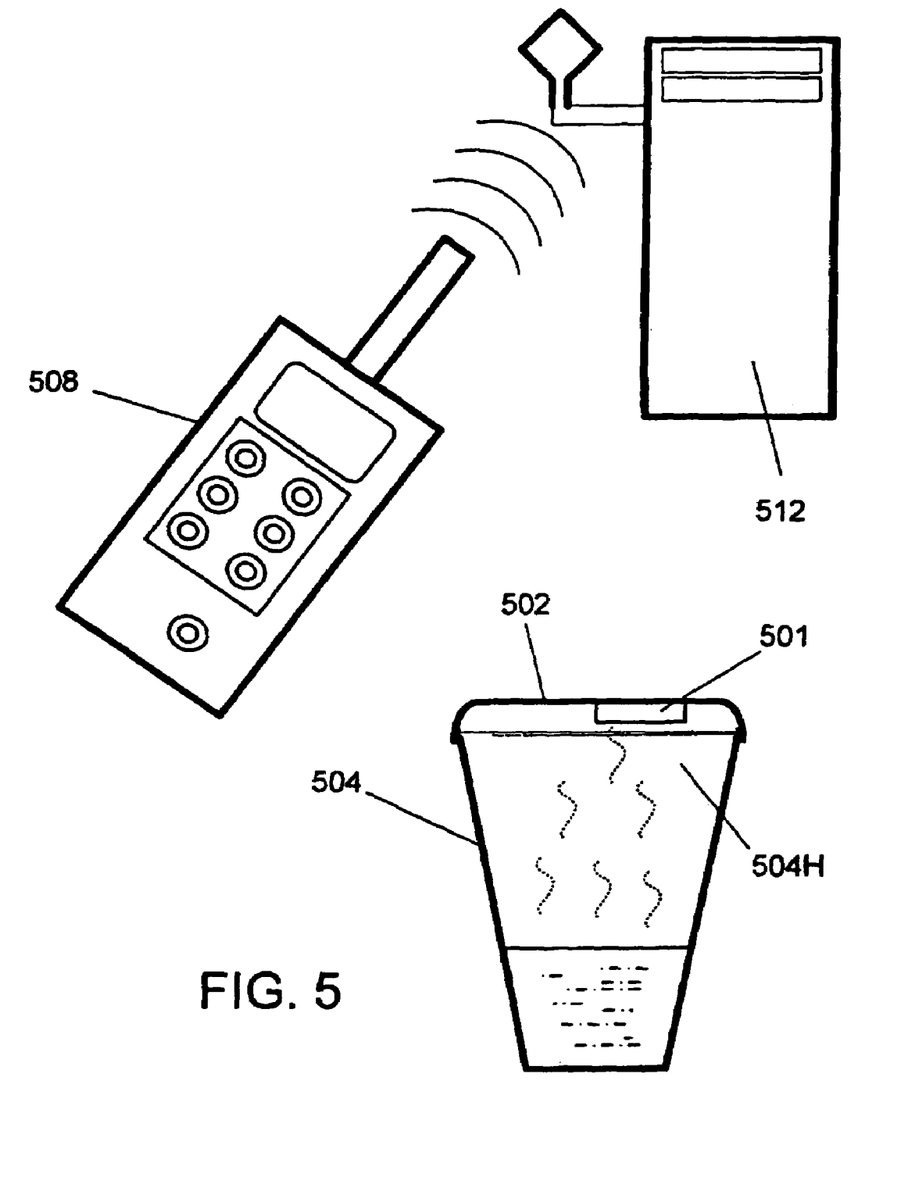
FIG. 5 is a view showing an interrogator collecting data such as from a bar code or the like via the use of an optional optical reader which can be collated with the data derived from the sensor arrangement within the container.

FIG. 5 depicts a situation wherein the interrogator 508 is configured to collect data in the manner shown in either of FIGS. 3 and 4 and to relay this data to a host arrangement 512 which can be more distal from the interrogator 508 than the samples and the sensor unit or units 501. While each interrogator 508 can be capable of analyzing the collected data, its size enables it to carry a power supply which would enable transmissions over relatively large distances and thus provide the ability to pass on the collected data to a host such as that located in a tactical command center. This, of course, would enable teams of investigators, each having their own interrogators, to work simultaneously and separately and wirelessly report sampling data back in manner which would allow the centralized, high speed collation and analysis of multiple data sets.

While the present invention has been described with reference to only a limited number of embodiments, as will be understood by those of skill in the art, the present invention which relates to an improved chemical sensing system using a passive chemical sensor unit, may be embodied in other specific forms without departing from the essential characteristics thereof.

For example, the interrogation unit and the sensing unit may communicate over any suitable frequency range, using any suitable one or more antenna designs. Furthermore, the container may be of any size and made of any suitable material to hold the sample, or more than one container may be used with the chemical sensing system described above. In addition, the interrogator unit/device need not be portable/handheld and may take the form of a stationary unit which is provided with a conveyor (for example) to transport the sealed container(s) thereby.

Accordingly, the foregoing disclosure is intended to be illustrative, but not limiting, of the ranges and scopes of the invention, which is set forth in the following claims.

What is claimed is:

1. A sensor arrangement comprising:
    a container configured to be environmentally sealed and to hold a chemical analyte;
    an interrogation unit which is separate from the container and operable to wirelessly transmit an interrogation signal and to wirelessly receive a response;
    a sensor array unit in fluid communication with the analyte disposed within the container, the sensor array unit being configured to analytically respond to a chemical characteristic of the analyte; and
    a responder unit connected with the sensor array unit, the responder unit being configured to be powered by the interrogation signal, the responder unit being operable to wirelessly transmit to the interrogation unit a signal indicative of the sensor array unit's response to the analyte,
    wherein the container has an upper portion and wherein the sensor array is provided on the upper portion,
    wherein the responder unit includes a dual antenna that is configured to receive signals at a first frequency band and to transmit signals at a second frequency band different from the first frequency band.

2. The sensor arrangement of claim 1, wherein the upper portion corresponds to a lid of the container.

3. The sensor arrangement of claim 1, wherein the sensor array is supported by the upper portion.

4. The sensor arrangement of claim 1, wherein the sensor array unit and the interrogation unit each include a memory circuit configured to store information obtained by the sensor array.

5. The sensor arrangement of claim 1, wherein the interrogation unit further includes an input subunit that is used to communicate information from the user.

6. A sensing method, comprising:

closing a container and enclosing a sensor array therein such that the sensor array is analytically exposed to vapor from the sample so as to be analytically exposed thereto;

using an interrogation unit which is separate from the container to wirelessly transmit an interrogation signal to a responder unit operatively connected with the sensor array, wherein the interrogation signal powers the responder unit;

generating a response indicative of the sample as sensed by the sensor array;

wirelessly transmitting the response to the interrogation unit using the responder unit; and providing information to a user from the interrogation unit by way of an output subunit included in the interrogation unit;

receiving the interrogation signal by a dual antenna of the responder unit at a first frequency band; and transmitting the response from the dual antenna of the responder unit at a second frequency band different from the first frequency band, wherein the sensor array is provided on an upper portion of the container.

7. The method of claim 6, further comprising supporting the sensor array by the upper portion of the container.

8. The method of claim 6, wherein the upper portion corresponds to a lid of the container.

9. The method of claim 6, further comprising:

storing, in a memory circuit included with the interrogation unit and the sensor array unit, information obtained by the sensor array.

10. The method of claim 6, further comprising:

providing information from the user to the interrogation unit by way of an input subunit included in the interrogation unit.

* * * * *